United States Patent [19]

Tzai et al.

[11] Patent Number: 5,034,486
[45] Date of Patent: Jul. 23, 1991

[54] TERPOLYMERS OF MALEIC ANHYDRIDE, $C_1$–$C_5$ ALKYL VINYL ETHER AND A $C_{12}$–$C_{14}$ ALPHA-OLEFIN, AND CROSSLINKED PRODUCTS THEREOF

[75] Inventors: Mohammed Tzai, Wayne; Krystyna Plochocka, Scotch Plains, both of N.J.; Yoon T. Kwak, Brooklyn, N.Y.; Thomas Rizzo, Cary, N.C.

[73] Assignee: GAF Chemicals Corporation, Wayne, N.J.

[21] Appl. No.: 564,920

[22] Filed: Aug. 9, 1990

[51] Int. Cl.$^5$ .................. C08F 222/04; C08F 216/12; C08F 236/00; C08F 210/14
[52] U.S. Cl. .................................... 526/271; 526/332; 526/348.3; 526/337
[58] Field of Search ........................................ 526/271

[56] References Cited

U.S. PATENT DOCUMENTS 4,280,979  7/1981  Dunleavy et al. ................. 264/157
4,370,454  1/1983  Messmer et al. ..................... 526/88
4,371,676  2/1983  Hoene .................................. 526/76

Primary Examiner—Joseph L. Schofer
Assistant Examiner—Wu C. Cheng
Attorney, Agent, or Firm—Walter Katz; Marilyn J. Maue; Joshua J. Ward

[57] ABSTRACT

Terpolymers of maleic anhydride, a $C_1$–$C_5$ alkyl vinyl ether and a $C_{12}$–$C_{14}$ alpha-olefin, and crosslinked products thereof, are provided herein for use in thickener, adhesive, sunscreen, hair spray, and waterproofing compositions. The alpha-olefin comonomer is a hydrophobic, straight chain, unsaturated hydrocarbon such as dodecene or tetradecene, which is present in the terpolymer in predetermined amounts relative to the hydrophilic maleic anhydride component, to provide a terpolymer having a suitable HLB for these applications.

6 Claims, No Drawings

TERPOLYMERS OF MALEIC ANHYDRIDE, $C_1$-$C_5$ ALKYL VINYL ETHER AND A $C_{12}$-$C_{14}$ ALPHA-OLEFIN, AND CROSSLINKED PRODUCTS THEREOF

BACKGROUND OF THE INVENTION

1. Field of the Invention

This invention relates to terpolymers of maleic anhydride, a $C_1$-$C_5$ alkyl vinyl ether and a $C_{12}$-$C_{14}$ alpha-olefin, and to crosslinked products thereof, which are provided within predetermined compositional ranges for application in adhesive, sunscreen, hair spray and waterproofing compositions, and for effective compatibility with organic solvents.

2. Description of the Prior Art

Copolymers of maleic anhydride and alkyl vinyl ethers are well known in the art and are conventionally prepared by free radical precipitation polymerization of the monomer mixture in an aromatic hydrocarbon solvent such as benzene in the presence of a protective colloid. Another method involves copolymerization of maleic anhydride, an alkyl vinyl ether and/or a $C_3$-$C_{10}$ alkene in contact with a powder bed. In the latter method, disclosed in U.S. Pat. No. 4,370,454, a large excess of the alkyl vinyl ether and/or alkene, e.g. 3 to 25, preferably 5 to 5, moles thereof, per mole of maleic anhydride monomer, is present during the polymerization, instead of the usual 1:1 mole ratio required of the copolymer. In the powder bed method, the heat generated during polymerization is removed by evaporating the excess alkyl vinyl ether and/or alkene which boils at a lower temperature than maleic anhydride. The examples in this patent were directed to copolymers of maleic anhydride and alkyl vinyl ethers, or copolymers of maleic anhydride and alkene.

Accordingly, iot is an object of this invention to provide new and improved terpolymers, and crosslinked products thereof, by an economical process.

SUMMARY OF THE INVENTION

What is provided herein are terpolymers of maleic anhydride (MA), a $C_1$-$C_5$ alkyl vinyl ether (AVE) and a $C_{12}$-$C_{14}$ alpha-olefin (AO), and crosslinked products thereof, for use in thickener, adhesive, sunscreen, hair spray and waterproofing compositions. Suitably, the molar ratio of MA:AVE:AO in the terpolymer is about 1:0.90–0.99:0.01–0.10, preferably about 1:0.94–0.96:0.04–0.06, respectively. Representative $C_1$-$C_5$ alkyl vinyl ethers include methyl vinyl ether, propyl vinyl ether and butyl vinyl ether. Suitable $C_{12}$-$C_{14}$ alpha-olefins are straight chain unsaturated hydrocarbons such as dodecene and tetradecene. Crosslinked products of such terpolymers with such crosslinking agents as 1,7-octadiene and 1,9-decadiene also are provided herein.

The terpolymers products of the invention are particularly characterized by a predetermined ratio between the hydrophobic, straight chain unsaturated $C_{12}$-$C_{14}$ hydrocarbon component and the hydrophilic, maleic anhydride component, which ratio affords a suitable hydrophilic-lipophilic balance (HLB) for the terpolymer and its crosslinked derivative.

A preferred process for making the terpolymers of the invention also is characterized in that the monomers are polymerized in a mixed solvent comprising a cycloaliphatic hydrocarbon such as cyclohexane and an aliphatic carboxylic ester such as ethyl acetate.

DETAILED DESCRIPTION OF THE INVENTION

In accordance with the present invention, there is provided terpolymers of maleic anhydride, a $C_1$-$C_4$ alkyl vinyl ether and a $C_{12}$-$C_{14}$ alpha-olefin within predetermined compositional ranges, and crosslinked products thereof, which terpolymers are useful in commercial application, and a process for making such terpolymers.

In this process, a suitable reactor is provided with appropriate inlet tubes, agitation means, and heater and temperature control means. The reactor is first purged with nitrogen to remove air from the system. Generally three separate purges are employed, at about 3 bars pressure and about 40° C. The reactor is precharged with maleic anhydride and the crosslinking agent in a suitable solvent which may be an aromatic hydrocarbon such as benzene or toluene but is preferably a mixed solvent of a cycloaliphatic hydrocarbon such as cyclohexane and an ester of an aliphatic carboxylic acid such as ethyl acetate. A solvent system which is a 50:50 mixture of cyclohexane and ethyl acetate is preferred.

The precharged reactor is purged with nitrogen at about 58° C. and a free-radical polymerization initiator is introduced in three stages during the polymerization, generally at the beginning, after about 1-½ hours and finally after about 3 hours, for a polymerization period of about 3 hours. Alternately, the initiator can be introduced in a continuous manner, e.g. as a solution in the reaction solvent. Any suitable initiator known in the art may be used including but not limited to peroxides. Tertiary butyl or tertiary amylperoxy pivalate are preferred. The concentration of initiator may vary widely, although suitably the initiator comprises about 0.05 to 2% by weight of the maleic anhydride reactant.

Then, simultaneously with feeding of initiator, the alkyl vinyl ether and alpha-olefin monomers are introduced separately or together into the precharged reactor, and at a controlled rate, during the course of the polymerization.

Overall, the molar ratio of maleic anhydride to the combined alkyl vinyl ether and alpha-olefin monomers in the process is set at about less than 1:1. In practice about a 10% excess of the alkyl vinyl ether over the 1:1 ratio is used to ensure complete conversion of the maleic anhydride to the terpolymer. The molar amount of $C_{12}$-$C_{14}$ alpha-olefin present in the resultant terpolymer is about 0.01–0.10, preferably 0.04–0.06. The crosslinker, when present, corresponds to about 5 wt. % of total monomers in the terpolymer. The predetermined amount of hydrophobic $C_{12}$-$C_{14}$ alpha-olefin in the terpolymer will provide terpolymers with a suitable HLB for various commercial applications.

Of course, during the polymerization, the reaction mixture is agitated effectively, and, at the conclusion of the polymerization, the reaction product is held at the polymerization temperature for about 1-½ hours. Then excess alkyl vinyl ether is vented and the product is discharged, filtered and the fine powders of the terpolymer is dried.

EXAMPLE 1

Preparation of Terpolymer of Invention 98 g. (1.00 mole) of maleic anhydride (MA) and 21.04 g. (0.125 mole) of dodecene (DD) in 534 g. of toluene was precharged in a reactor equipped with suitable inlet tubes, agitation means, and heater and temperature control means, and the reactor was purged three times with nitrogen at 50 psi nitrogen pressure at 58° C. Then 3.92 g. (4 wt. % on MA) of Lupersol 11 in 15 g. of toluene was added at a rate of 9.9 ml/min. Simutaneously, 55.12 g. (72.13 ml) (0.95 mole) of methyl vinyl ether (MVE) was fed into the reactor over a period of 4 hours while agitating the reaction mixture at about 280 rpm. The reactant monomers corresponds to 23% solids in this solvent system. The reactor was held at 58° C. for 1 hour, cooled, excess methyl vinyl ether was vented, the product was discharged from the reactor, filtered, washed, and dried.

A solid product was obtained which had a molar ratio of maleic anhydride to methyl vinyl ether to dodecene (MA:MVE:DD) of about 1.0:0.95:0.05. The yield was 147.3 g. (91.2%). The specific viscosity was 0.15 as measured in 1% methyl ethyl ketone, viscometer I 616, size 100.

Preparation of Crosslinked Terpolymers of Invention

EXAMPLE 2

60.0 g. (0.612 mole) of maleic anhydride was precharged into a reactor with 4.78 g. (0.343 mole) of tetradecene, 4.78 g. (0.0434 mole) of 7-octadiene and 420 g. of a 50:50 mixture of cyclohexane and ethyl acetate. The reactor was purged with nitrogen and heated to 58° C. Then a mixture of 39.09 g. (50.88 ml., 0.365 mole) of methyl vinyl ether was admitted into the reactor slowly over a period of 3 hours. Simultaneously, three portions of 0.1 g. each (0.5% based on MA) of Lupersol 11 were admitted during the polymerization. After 3 hours, the reaction product was held at 58° C. for 1-½ hours, cooled to room temperature, excess methyl vinyl ether vented and the product was discharged, filtered and dried to provide a fine, dry crosslinked terpolymer product.

The crosslinked terpolymer comprised a molar ratio of maleic anhydride to methyl vinyl ether to tetradecene (MA:MVE:TD) of about 1.0:0.96:0.04 and was crosslinked with 5.0% by weight of 1,7-octadiene based on the total weight of the terpolymer.

EXAMPLE 3

The terpolymer was crosslinked with other crosslinking agents selected from dienes, divinyl ethers and allyl carbohydrates with similar results.

EXAMPLE 4

The 1,7-octadiene crosslinker was introduced with the externally fed monomers. The reaction product slurry was thick but filterable, and it was dried at 65° C. in vacuum oven.

The crosslinked terpolymers prepared above found particular application in thickener, adhesive, sunscreen, hair spray and waterproofing compositions.

While the invention has been described with particular reference to certain embodiments thereof, it will be understood that changes and modifications may be made which are within the skill of the art. Accordingly, it is intended to be bound only by the following claims, in which:

What is claimed is:

1. A terpolymer of maleic anhydride, a $C_1$-$C_5$ alkyl vinyl ether and a $C_{12}$-$C_{14}$ alpha olefin in the molar ratio of about 1.0:0.90–0.99:0.01–0.10 which is crosslinked with a crosslinking agent.

2. A crosslinked terpolymer of claim 1 wherein said crosslinking agent is 1,7-octadiene.

3. A crosslinked terpolymer of claim 1 wherein said crosslinking agent is present in an amount of about 4–6 wt. % of the monomers in the terpolymer.

4. A crosslinked terpolymer of claim 1 wherein said alpha-olefin is a straight chain $C_{12}$-$C_{14}$ hydrocarbon.

5. A process for preparing the crosslinked terpolymer of claim 1 which comprises polymerizing the monomers in a solvent system of cyclohexane and ethyl acetate.

6. A process according to claim 5 wherein said solvent system is a 50:50 mixture of cyclohexane and ethyl acetate.

* * * * *